United States Patent [19]

Garcia et al.

[11] Patent Number: 5,000,046
[45] Date of Patent: Mar. 19, 1991

[54] METHOD OF MEASURING A LIQUID POOL VOLUME

[75] Inventors: Gabe V. Garcia, Las Cruces, N. Mex.; Nancy M. Carlson; Alan D. Donaldson, both of Idaho Falls, Id.

[73] Assignee: The United States of America as represented by the United States Department of Energy, Washington, D.C.

[21] Appl. No.: 478,375

[22] Filed: Feb. 12, 1990

[51] Int. Cl.$^5$ .............................................. G01F 22/00
[52] U.S. Cl. ................................. 73/597; 73/290 V; 73/657; 73/643
[58] Field of Search ............... 73/655, 657, 290 X, 73/597, 605, 643, 592, 149; 374/54, 142; 367/908

[56] References Cited

U.S. PATENT DOCUMENTS

| | | | |
|---|---|---|---|
| 4,578,997 | 4/1986 | Soltz | 73/290 V |
| 4,659,224 | 4/1987 | Monchalin | 73/657 |
| 4,837,750 | 6/1989 | Saunders | 73/290 V |

OTHER PUBLICATIONS

Parker et al., Journal of Applied Physics, vol. 58, 11 (Dec. 1985), pp. 4150–4164.
Dewhurst et al., Journal of Applied Physics, vol. 63, 4 (Feb. 15, 1988), pp. 1225–1227.

Primary Examiner—Hezron E. Williams
Assistant Examiner—Rose M. Finley
Attorney, Agent, or Firm—Thomas G. Anderson; Robert J. Fisher; William R. Moser

[57] ABSTRACT

A method of measuring a molten metal liquid pool volume and in particular molten titanium liquid pools, including the steps of (a) generating an ultrasonic wave at the surface of the molten metal liquid pool, (b) shining a light on the surface of a molten metal liquid pool, (c) detecting a change in the frequency of light, (d) detecting an ultrasonic wave echo at the surface of the molten metal liquid pool, and (e) computing the volume of the molten metal liquid.

7 Claims, 3 Drawing Sheets

METHOD OF MEASURING A LIQUID POOL VOLUME

CONTRACTUAL ORIGIN OF THE INVENTION

The U.S. Government has rights in this invention pursuant to Contract No. DE-AC07-76ID01570 between the United States Department of Energy and EG&G Idaho, Inc..

BACKGROUND OF THE INVENTION

The present invention relates to a method of measuring the volume of molten metal liquid pools and in particular noncontacting laser ultrasonic generation and detection at the surface to measure the volume of molten titanium liquid pools.

Currently, vacuum arc remelting is used to produce much of the nation's titanium from Kroll process sponge. However, the process provides only a limited means of removing oxynitride and carbide inclusions from the melt, which can become stress intensifiers in the ingot. An improved quality of the melted product will result in less scrap, and provide industry with the ability to recycle scrap into high value products. The most important aspect, is the capability to produce superior ingots with the potential for designing turbine engines and the like incorporating titanium to be lighter and more efficient.

Plasma and Electron beam hearth melting have the potential to eliminate these stress-intensifying inclusions by increasing the residence time of the molten titanium in the hearth so that the oxynitrides dissolve and the carbides settle out of the melt. These new processes have caused a critical need for an accurate means to measure the volume of the molten metal during hearth melting processes.

At the high operating temperatures of the titanium hearth (1650° c) existing contacting sensors are not practical, and are also a source of melt contamination. Therefore, a noncontacting sensor method using ultrasound wave echo was developed to determine the depth of the titanium melt, which required only melt surface access.

Several types of optical laser-based ultrasonic detectors have been developed for noncontacting measurement of surface motion due to ultrasonic waves. In some cases these devices have been employed at high temperatures to record material properties during heating. However, the majority of these systems depend on phase sensitive detection of the light and require polished surfaces and strict alignment for adequate signal-to-noise ratio, and thus are not suitable for plasma and electron beam hearth melting processes.

It is therefore an object of this novel method to provide a noncontacting means to accurately measure the volume of a molten metal liquid, and further another object of this novel method is to provide a means to accurately measure the volume of molten metal liquid pools without causing a source of melt contamination.

Additional objects, advantages and novel features of the method will be set forth in part in the description which follows, and in part will become apparent to those skilled in the art upon examination of the following or may be learned by practice of the novel method. The objects and advantages of the method may be realized and attained by means of the instrumentalities and combinations particularly pointed out in the appended claims.

To achieve the foregoing and other objects and in accordance with the purpose of the present invention, as embodied and broadly described herein, the novel method of measuring a molten liquid pool volume may comprise the steps of (a). generating an ultrasonic wave echo at the surface of the molten liquid pool; (b). shining a on the surface of the pool; (c). detecting the change in frequency of the light; (d). detecting the ultrasonic wave echo as it reflects at the surface of the pool, after it reflects off the bottom of the molten metal liquid pool; and e). computing the volume of the molten liquid pool by using the frequency change in the light and the time elapsed for the ultrasonic wave echo to reflect off the bottom of the molten metal liquid pool, and return to the surface of the pool.

SUMMARY OF THE INVENTION

The present invention relates to a method of measuring a molten metal liquid pool and in particular a method of measuring molten titanium during hearth melting.

The present invention allows for the critical measurement of the volume of molten titanium metal to ensure sufficient residence time in the melt. It is accomplished by generating an ultrasonic wave echo at the surface of the molten titanium metal pool. A laser or equivalent may be used to generate an ultrasonic wave echo that travels through the molten titanium to the bottom surface and is reflected back to the top surface of the molten titanium. Simultaneously, a light is shined on the surface of the molten titanium and as the ultrasonic wave echo returns to the surface of the molten titanium it causes a displacement in the surface of the pool. This causes a change in the frequency of the light being shined on the surface of the molten titanium, allowing for the returning ultrasonic wave echo to be detected by a detection device, preferably an interferometer. A Fabry-Perot interferometer was chosen as the detector in this work because this unit has proven to be sensitive to a change in the frequency of light scattered off the surface. Thus, light can be collected from a diffuse surface and processed with this unit to yield the velocity of the surface of a molten liquid metal. The primary requirement is that a sufficient amount of scattered light be collected and passed through the interferometer. This is accomplished by using as a light source a laser capable of delivering a sufficient amount of light to achieve an acceptable signal-to-noise ratio.

Having predetermined the volume equation of the hearth and calculated the velocity of sound in the molten metal at the appropriate operating temperature, the change in the frequency of the light and the recorded time of the ultrasonic wave echo to reflect off the bottom of the liquid pool can be used to calculate the volume of the molten metal liquid pool.

BRIEF DESCRIPTION OF THE DRAWINGS

The accompanying drawings, which are incorporated in and form a part of the specification, illustrate the present invention and, together with the description, serve to explain the principles of the invention. In the drawings.

DETAILED DESCRIPTION OF THE INVENTION

Figure 1:
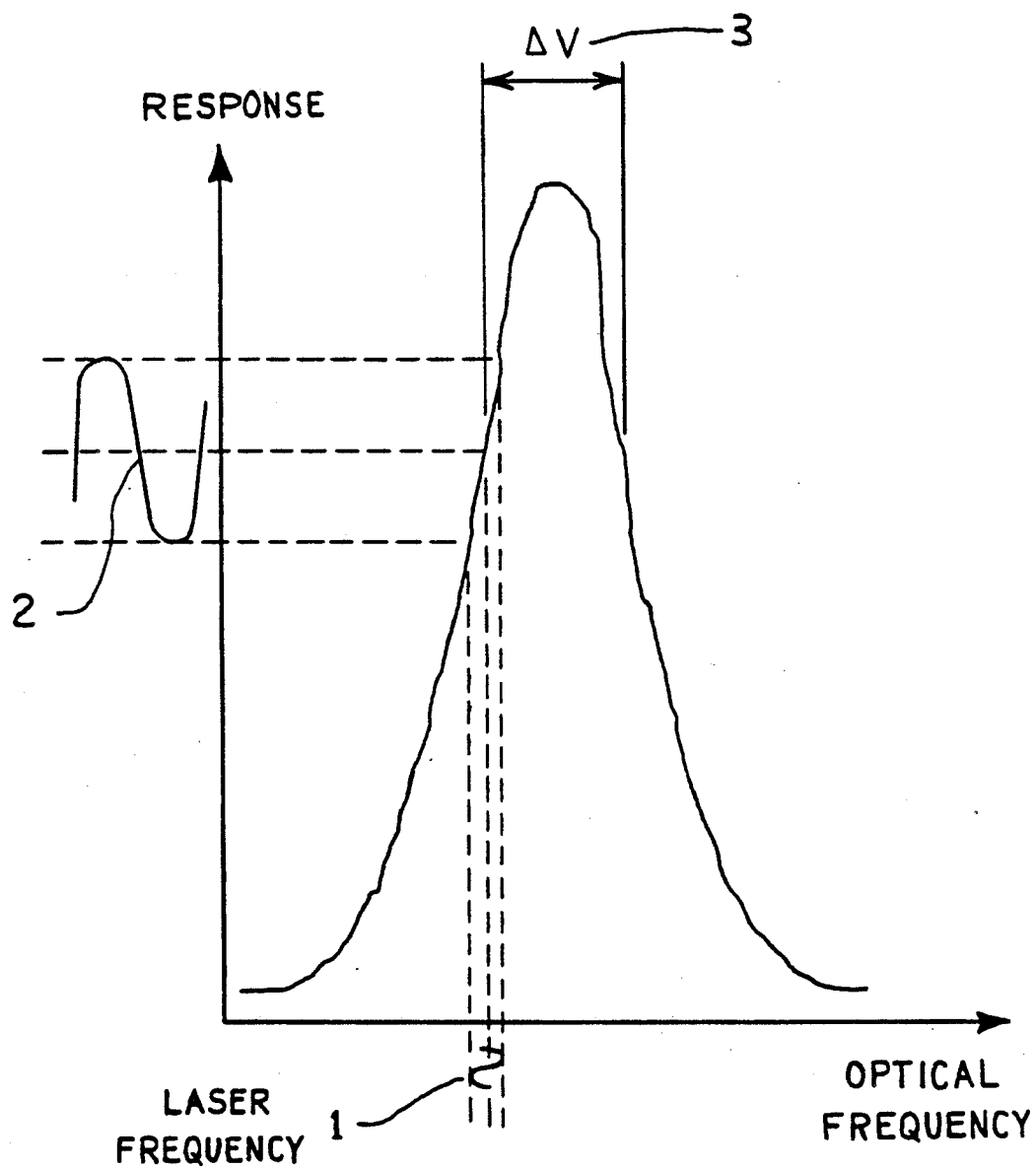
FIG. 1 shows the frequency response of the Fabry-Perot Interferometer.
Figure 2:
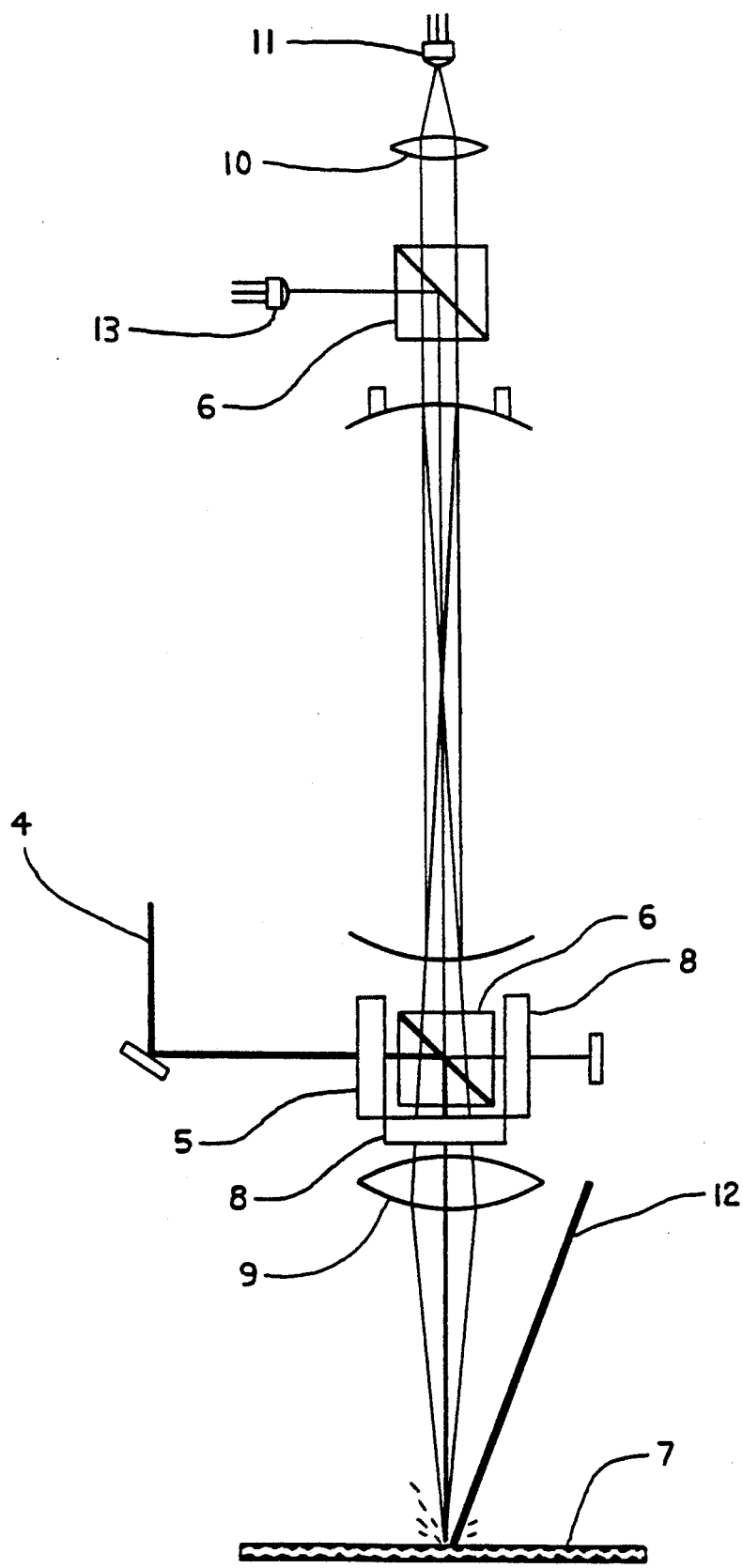
FIG. 2 is a schematic of the detection system using the Fabry-Perot Interferometer.

Referring to FIGS. 1 and 2, in FIG. 1 a Fabry-Perot interferometer frequency response is shown. The oscillating molten metal surface causes the reflected or scattered light to be Doppler shifted in frequency as indicated at 1. This light can be demodulated by passing it through an interferometer. Demodulation is accomplished by setting the interferometer at the mid-point of its response peak shown at position 2, thus giving an output intensity proportional to the Doppler frequency shift of the scattered or reflected light, and hence proportional to the change in velocity of the molten metal surface as indicated at 3.

A schematic of the detection system is shown in FIG. 2. A 1-W argon ion laser beam 4 is divided into two beams using a ½ wave plate 5 and a polarizing beam splitter cube 6. Part of the light goes to the molten metal surface 7 for the detection of an ultrasonic wave echo, while the rest is directed to a reference photodiode 13 to position the interferometer frequency response so that the laser frequency is at the operating point 2, near the half maximum of the curve. This has been found to provide the highest sensitivity for detecting a change in frequency of light with the Fabry-Perot interferometer. The two beams are kept separate using the beam splitter cubes 6 and ¼ wave plates 8. A collection lens 9 is used to capture scattered light off the molten metal surface 7. The light then travels through the interferometer where it is demodulated and through a lens 10 that focuses the light onto a signal photodiode 11 used to detect the ultrasonic wave echo. A ND:YAG Pulsed laser 12 is used to generate the ultrasonic wave echo at the molten metal surface 7.

Figure 3:
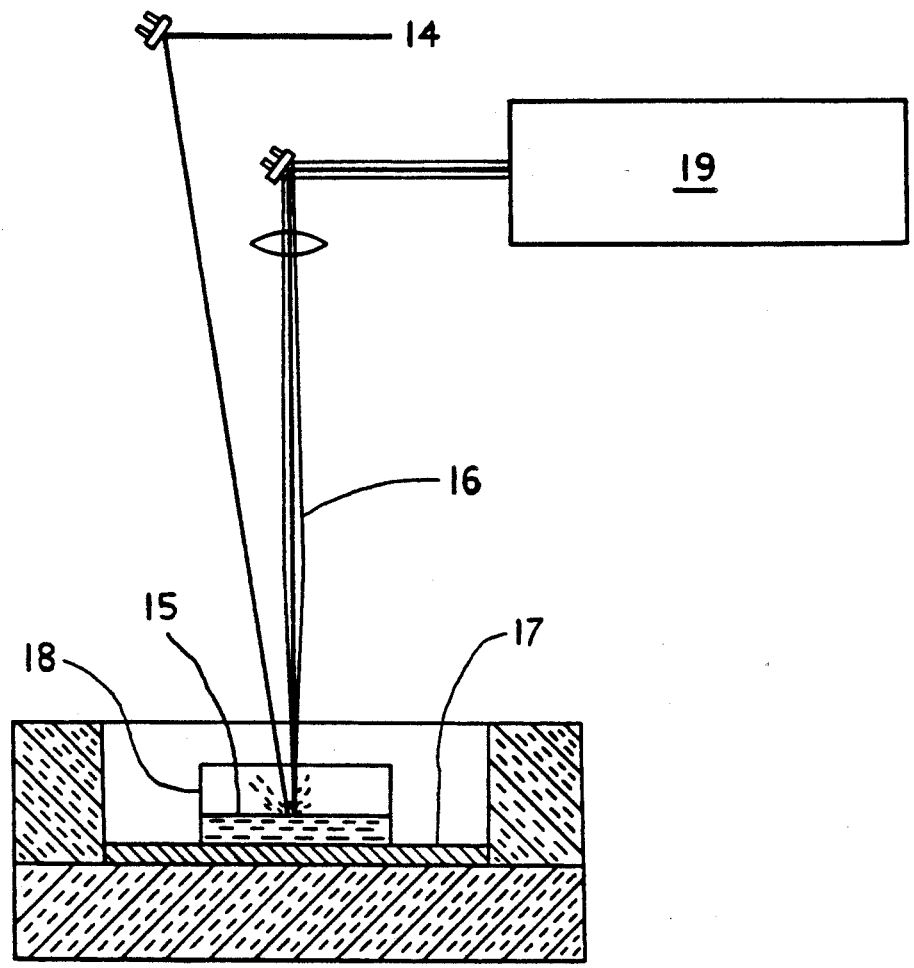
FIG. 3 shows another embodiment of a detection system using a pulsed laser to produce an ultrasonic wave echo.

FIG. 3, shows another apparatus for affecting the invention which uses a 100 mJ/pulse ND:YAG pulsed laser 14 to produce a longitudinal wave echo that travels through the molten tin to the bottom surface and back to the top surface. A Fabry-Perot interferometer 19 detects the longitudinal wave at the surface of the molten tin 15 by using an argon laser 16 as a light source. A resistive furnace 17 coupled with a temperature controller is used to maintain the tin in a molten state. The volume equation of the container 18 is predetermined, as well as, the velocity of sound having been determined for molten liquid tin at the operating temperature measured by using a thermocouple.

When considering the above, it is understood that the novel method can be accomplished with the apparatus disclosed, as well as, with various changes in the arrangement without departing from the scope and spirit of the method.

The embodiments of the invention in which an exclusive property or privilege is claimed are defined as follows:

1. A method of measuring a molten metal liquid pool volume, comprising the steps of:
   (a) shining a detection light on the surface of a molten metal liquid pool;
   (b) generating an ultrasonic wave echo at the surface of said molten metal liquid pool, with a generating light to cause a change in frequency of said detection light;
   (c) detecting a change in the frequency of said detection light at the surface of said molten metal liquid pool;
   (d) detecting said ultrasonic wave echo at the surface of said molten liquid pool, after it reflects off the bottom of said molten metal liquid pool; and
   (e) computing the volume of the molten liquid pool by using the change in the frequency of said light and the time elapsed from generating said ultrasonic wave echo at the surface of said molten metal liquid pool and detecting the ultrasonic wave echo off the bottom of said molten liquid pool.

2. A method of measuring a molten metal liquid pool volume as recited in claim 1 wherein:
   said step of shining a detection light on said surface of said molten metal liquid pool is generated by a laser beam split into two beams by a polarized beam splitter cube.

3. A method of measuring a molten metal liquid pool volume as recited in claim 2 wherein;
   said step of generating an ultrasonic wave echo is accomplished by a laser.

4. A method of measuring a molten metal liquid pool volume as recited in claim 3 wherein:
   said step of detecting the frequency change of said light is accomplished by using an interferometer.

5. A method of measuring a molten metal liquid pool volume as recited in claim 4 wherein:
   said step of detecting said ultrasonic wave echo, after it reflects off the bottom of said molten metal liquid pool, is determined by the effects of the ultrasonic wave echo as it returns to the surface of the molten metal liquid pool, which causes motion at the surface of said molten metal liquid pool, causing said detection light to change frequency at the surface of said molten metal liquid pool.

6. A method of measuring a molten metal liquid pool volume as recited in claim 5 wherein:
   said step of computing the volume of the molten liquid pool by using the change in the frequency of said light and the time elapsed in detecting said ultrasonic wave echo off the bottom of said molten metal liquid pool includes, multiplying the velocity of sound of the molten liquid metal by the time elapsed in detecting said ultrasonic wave echo off the bottom of said molten metal liquid pool.

7. A method of measuring a liquid pool volume, comprising the steps of:
   (a) shining a detecting light on the surface of a liquid pool;
   (b) generating an ultrasonic wave echo at the surface of said liquid pool, with a generating light to cause a change in frequency of said detection light;
   (c) detecting a change in the frequency of said light at the surface of said signal pool;
   (d) detecting said ultrasonic wave echo the surface of said liquid pool, after it reflects off the bottom of said liquid pool; and
   (e) computing the volume of the liquid pool by using the change in the frequency of said light and the time elapsed from generating said ultrasonic wave echo at the surface of said molten metal liquid pool and detecting the ultrasonic wave echo off the bottom of said liquid pool.

* * * * *